(12) United States Patent
Elmaleh et al.

(10) Patent No.: US 7,060,251 B1
(45) Date of Patent: Jun. 13, 2006

(54) IMAGING AGENTS FOR EARLY DETECTION AND MONITORING OF CARDIOVASCULAR PLAQUE

(75) Inventors: David R. Elmaleh, Newton, MA (US); Alan J. Fischman, Boston, MA (US); John W. Babich, Scituate, MA (US)

(73) Assignee: The General Hospital Corporation, Charlestown, MA (US)

( * ) Notice: Subject to any disclaimer, the term of this patent is extended or adjusted under 35 U.S.C. 154(b) by 0 days.

(21) Appl. No.: 09/530,818

(22) PCT Filed: Sep. 8, 1998

(86) PCT No.: PCT/US98/18685

§ 371 (c)(1),
(2), (4) Date: Jan. 9, 2002

(87) PCT Pub. No.: WO99/12579

PCT Pub. Date: Mar. 18, 1999

(51) Int. Cl.
*A61K 49/04* (2006.01)
(52) U.S. Cl. ............. 424/9.4; 424/1.11; 424/1.65; 424/9.1; 424/1.89; 424/1.85; 424/1.81
(58) Field of Classification Search ............. 424/1.11, 424/1.65, 1.69, 1.49, 1.73, 1.81, 9.1, 1.85, 424/1.89, 9.3, 9.4, 9.5, 9.7, 9.6, 9.8; 206/223, 206/569, 570; 534/7, 10–16
See application file for complete search history.

(56) References Cited

U.S. PATENT DOCUMENTS

| | | | | |
|---|---|---|---|---|
| 5,175,343 A | * | 12/1992 | Fritzberg et al. | 560/145 |
| 5,364,612 A | * | 11/1994 | Goldenberg | 424/1.53 |
| 5,744,120 A | * | 4/1998 | Edwards et al. | 424/1.65 |
| 6,025,477 A | * | 2/2000 | Calenoff | 530/388.2 |
| 6,299,857 B1 | * | 10/2001 | Elmaleh et al. | 424/1.73 |
| 6,331,287 B1 | * | 12/2001 | Conti et al. | 424/1.89 |

FOREIGN PATENT DOCUMENTS

| | | |
|---|---|---|
| EP | 0 419 203 A1 | 3/1991 |
| WO | WO 90/10463 | 9/1990 |
| WO | WO 91/02547 | 3/1991 |
| WO | WO 93/12819 | 7/1993 |
| WO | WO 95/03280 | 2/1995 |
| WO | WO 95/06633 | 3/1995 |
| WO | WO 95/11045 | 4/1995 |
| WO | WO 96/31243 | 10/1996 |
| WO | WO 97/10853 | 3/1997 |

OTHER PUBLICATIONS

Babich and Fischman; "Effect of "Co-Ligand" on the Biodistribution of$^{99m}$Tc-labeled Hydrazino Nicotinic Acid Derivatized Chemotactic Peptides", Nucl. Med. Biol. 22(1): 25-30, (1995).
Dinkelborg et al.; "Molecular Imaging of Atherosclerosis Using a Technetium-99m-Labeled Endothelin Derivative", J. Nucl. Med. 39: 1819-1822, (1998).
Hom and Katzenellenbogen; "Technetium-99m-Labeled Receptor-Specific Small -Molecular Radiopharmaceuticals: Recent Developments and Encouraging Results", Nuclear Medicine & Biology 24: 485-498, (1997).
Liu et al; "99m Tc-labeling Kinetics of Four Thiol-Countaining Chelators and 2-Hydrazinopyridine: Factors Influencing Their Radiolabeling Efficiency", Appl. Radiat. Isot. 48(8): 1103-1111, ( 1997).
Mahmood et al., "A New Approach To Labeling Cells With Technetium-99m, Part I. Preparation of Modified Polylysine and In Vitro Cell Labeling", Nuclear Medicine and Biology 23: 79-85, (1996).
Vaidyananathan and Zalutsky; "Fluorine-18 Labeled Chemotactic Peptides: A Potential Approach for the PET Imaging of Bacterial Infection", Nuclear Medicine and Biology, 22 (6): 759-764, ( 1995).
Welling et al.; "Detection of Experimental Infections with$^{99m}$Tc-Labeled Monoclonal Antibodies Against TNF-α AND Interleukin-8", Nuclear Medicine & Biology 24: 649-655, (1997).
International Search Report Completed on Jan. 13, 1999 and Mailed on Feb. 1, 1999.

* cited by examiner

*Primary Examiner*—Dameron Jones
(74) *Attorney, Agent, or Firm*—Foley Hoag LLP

(57) ABSTRACT

The invention provides imaging agents comprising a label in association with a plaque specific targeting molecule. Methods for using the imaging agents to diagnose or monitor plaque formation and growth and kits containing the cardiovascular agents or components suitable for production of the imaging agents are also provided.

6 Claims, No Drawings

IMAGING AGENTS FOR EARLY DETECTION AND MONITORING OF CARDIOVASCULAR PLAQUE

RELATED APPLICATIONS

This application is a 371 of Application No. PCT/US98/18685, filed Sep. 8, 1998, which claims priority to U.S. application Ser. No. 08/925,213, filed Sep. 8, 1997, now abandoned.

The present invention is in the field of nuclear medicine. More specifically, the invention relates to imaging of plaque formation in cardiovascular tissue.

BACKGROUND OF THE INVENTION

It is estimated that more than 1.5 million myocardial infarctions occur annually in the United States, and at least 500,000 infarctions result in death, usually sudden. (American Heart Association, Heart and Stroke Facts. Dallas, Tex: American Heart Association National Center; 1992). Accordingly, myocardial infarction is the most frequent cause of mortality in the United States; and in most Western countries (Coopers, ES. Prevention: The Key to Progress. Circulation. 1993; 24: 629–632; WHO-MONICA Project. Myocardial Infarction and Coronary Deaths in the World Health Organization Monica Project: Registration Procedures, Event Rates and Care Fatality Rates in 38 Populations From 21 Countries in Four Continents. Circulation. 1994; 90:583–612). However, even the optimal use of thrombolytic therapy for myocardial infarction, the advance of which the greates attention has been focused, could prevent only 25,000 deaths or 5% of the total, because most deaths occur suddenly, before any type of treatment can be initiated. (Muller, J E, et al., Acute Risk Factors and Vulnerable Plaques: The Lexicon of a New Frontier. J. Am. Coll. Cardiol. 1994; 23:809–813).

In 1992, Fuster et al., (Fuster V. et al., The Pathogenesis of Coronary Artery Disease and the Acute Coronary Syndromes. N. Engl. J. Med. 1992; 326:242–250.) classified the progression of coronary atherosclerotic disease into five phases. Phase I is represented by a small plaque that is present in most people under the age of 30 years regardless of their country of origin and that usually progresses slowly (types I to III lesions). Phase 2 is represented by a plaque, not necessarily very stenotic, with a high lipid content that is very prone to rupture (types IV and Va lesions). The plaque of phase 23 may rupture with predisposition to change its geometry and to formation of mural thrombus, these processes by definition represent phase 3 (type I lesion), with a subsequent increase in stenosis, possibly resulting in angina, or ischemic sudden death. The mural and occlusive thrombi from plaques of phases 3 and 4, by being organized by connective tissue, may contribute to the progression of the atherosclerotic process represented by severely stenotic or occlusive plaques of phase 5 (types Vb and Vc lesions). The severely stenotic plaques of phase 5, by a phenomenon of stasis and/or deendothelialization, can become complicated by a thrombus and/or rapid myoproliferative response, also leading to an occlusive plaque of phase 5. Of interest, about two thirds of coronary occlusions are the result of this late stenotic type of plaque and are unrelated to plaque disruption. Unlike the rupture of less-stenotic lipid-rich plaques, leading to occlusion and subsequent infarction or other acute coronary syndromes, this process of occlusion from late stenotic plaques tends to be silent because the preceding severe stenosis and ischemia enhance protective collateral circulation. (Fuster, V et al., The Pathogenesis of Coronary Artery Disease and the Acute Coronary Syndromes. N. Engl. J. Med. 1992; 326:242–250; Chesebro, J H et al., Antithrombotic Therapy and Progression of Coronary Artery Disease. Circulation. 1992; 86 (suppl III)).

Sensitive and specific agents are needed to identify the early stages of plaque formation in a subject, the progression of which can then be delayed or reduced by initiation of an appropriate therapeutic regimen or change in lifestyle.

SUMMARY OF THE INVENTION

In general, the invention features imaging agents comprised of a targeting moiety and a label, such as a radionuclide or paramagnetic contrast agent. In preferred embodiments, the labeled imaging agents comprise small molecule that rapidly (i.e. less than about 24 hours, more preferably less than about 12 hours and most preferably less than about 6 hours) localize, selectively and irreversibly localize at the site of a plaque and rapidly clear from other tissue.

Examples of appropriate radionuclides include: $^{131}$I, $^{125}$I, $^{123}$I, $^{99m}$Tc, $^{18}$F, $^{68}$Ga, $^{67}$Ga, $^{72}$As, $^{89}$Zr, $^{64}$Cu, $^{62}$Cu, $^{111}$In, $^{203}$Pb, $^{198}$Hg, $^{97}$Ru, $^{11}$C and $^{201}$Tl. Suitable paramagnetic contrast agents include gadolinium, cobalt, nickel, manganese and iron. Particularly preferred radionuclides or paramagnetic contrast agents have an appropriate half-life and high specific activity.

Particularly preferred targeting moieties comprise components of the processes involved in plaque formation and growth as well as specific bind partners thereto (e.g. receptors and fragments thereof, receptor ligands, and antibodies and binding fragments thereof). Particularly preferred targeting moieties are comprised of components of processes involved in plaque formation and growth as well as specific partner to such components (e.g. receptors and fragments thereof, receptor ligands (e.g receptor agonists or antagonists), and antibodies and binding fragments thereof). Examples include: (i) cells, including smooth muscle cells, leukocytes, lymphocytes and (B-lymophocytes), monocytes, macrophages, foam cells, platelets, erythrocytes and polymorphonuclear cells (e.g. granulocytes and neutrophils) and cellular fragments (e.g. heme) and analogs thereof (e.g. porphoryins and phthalocyanines); (ii) molecules that attract or modify cellular migration including chemotactic proteins and peptides (e.g. monocyte chemotactic protein 1 (MCP-1) and N-formyl-methionyl-leucyl-phenalanine other formyl peptides; colony stimulating factors (e.g. GM-CSF and CSF-1 and receptors and antibodies thereto; and platelet factor 4 (iii) growth factors (e.g. transforming growth factors, e.g. TGF-β, endothelial growth factors (e.g. VEGF) and growth factors that initiate smooth muscle proliferation), (iii) adhesive cell-surface glycoproteins (e.g. E-selectin, VCAM-1 and VCAM1β and; and carbohydrates such as $^{11}$C-deoxy-D-glucose and $^{18}$F-2-fluorodeoxy-D-glucose); (iv) other components of a vascular inflammatory response (for examples complement components (e.g. C1, C1q, C1r, C1s, C2, C3, C3a, C3b, C4, C4C2, C4C2C3b, C5a, C5b and C5a), immunoglobulins and cytokines (e.g. interleukins (e.g. IL-1, (IL-1α and IL-1β, IL-2; IL-3; IL-6; IL-7; and IL-8) interferons (interferon α, interferon γ) and tumor necrosis factors (e.g. TNF-α); (v) cellular sources of energy for metabolically active plaque formation; (vi) lipids (e.g. liposomes, including polyethylene glycol (PEG) coated liposomes, cholesterol and its esters, lipoproteins (e.g. LDL, HDL, oxidized LDL) and lipid receptors; and (vii) components of the clotting cascade (e.g. fibrin, thrombin, fibrinogen, factor VIII, factor IX, etc.)

In another aspect, the invention relates to methods for making the imaging agents. In a preferred embodiment, an appropriate label is ionically or covalently associated with the targeting moity via any of a variety of means. In a preferred embodiment, the association is via incorporation of a chelating structure, such as —$N_2S_2$, —$NS_3$, —$N_4$, an isonitrile, a hydrazine, a HYNIC (hydrazinonicotinic acid), 2-methylthiolnicotinic acid, phosphorus, or a carboxylate containing group.

In yet another aspect, the invention features methods for imaging a subject for plaque formation and growth comprising administering to the subject an effective amount of an imaging agent of the invention and detecting the concentration and spatial distribution of the agent using an appropriate detection means, wherein a higher differential accumulation of the agent in a particular location relative to other locations within the cardiovascular tissue of a subject is indicative of plaque formation in the subject and wherein a higher differential accumulation of the agent in a particular location relative to the accumulation detected at the same location in a prior imaging is indicative of plaque growth.

In yet a further aspect, the invention features a kit for imaging which includes, but is not limited to, a supply of the imaging agent or its precursor. The kit may also include at least one chelating structure and/or an auxiliary molecule such as, mannitol, gluconate, glucoheptonate, and tartrate; and a tin containing reducing agent.

Other features or advantages of the present invention will be apparent from the following detailed description and from the claims.

DETAILED DESCRIPTION OF THE PREFERRED EMBODIMENTS

For convenience, the meaning of certain terms and phrases employed in the following specification, examples and appended claims are provided below:

An "antibody or fragment thereof" refers to a whole polyclonal or monoclonal antibody or a binding fragment therof.

A "chelating structure" refers to any molecule or complex of molecules which bind to both the label and targeting moiety. Examples include: $N_2S_2$ structure, an $NS_3$ structure, an $N_4$ structure, an isonitrile-containing structure, a hydrazine containing structure, a HYNIC (hydrazinonicotinic acid) group-containing structure, a 2-methylthiolnicotinic acid group-containing structure, a carboxylate group containing structure, and the like.

"Cardiovascular disease" or "cardiovascular lesion" refers to any of a variety of disease or lesions to the heart or vasculature of a subject. Examples include atherosclerosis (i.e. thickening and hardening of arteries due to plaque formation) and related disorders resulting from occluded blood flow (e.g. angina, cerebral ischemia, renal hypertension, ischemic heart disease, stroke) and thrombus and formation (e.g. Deep Vein Thrombosis (DVT)).

"Cardiovascular tissue" refers to any and all tissue comprising the cardiovascular system including: all components of the heart, aortas, arteries (e.g. coronary and carotid), veins, or components of these tissues and organs.

A "precursor of an imaging agent" refers to any molecule or complexes of molecules which are easily converted to the imaging agent.

A "small molecule" refers to a composition having a molecular weight, which is less than about 5KD, more preferably less than about 4KD, even more preferably less than about 3KD and most preferably less than about 2 KD.

"Subject" refers to an animal, e.g. mammal, particularly a human.

A "targeting moiety or precursor thereof" is any molecule or biological entity that targets cardiovascular tissue or thrombi, or any molecule or biological entity that is easily converted to such a molecule or biological entity.

"thrombus" refers to a clot of blood formed within a blood vessel from a plaque and which remains attached to its place of origin.

"vascular inflammation" refers to vascular tissue damage in a subject, which may result from a number of causes (e.g. microbial infection, autoimmune processes, any injury or trauma, etc). Regardless of cause, the vascular inflammatory response consists of a complicated set of functional and cellular adjustments involving changes in microcirculation, movement of fluids, proliferation of smooth muscle cells, generation of foam cells and influx and activation of inflammatory cells.

The present invention provides novel imaging agents which are comprised of a targeting moiety and a label. These novel imaging agents specifically accumulate in actively forming or actively growing plaques and therefore are useful for detecting or monitoring plaque formation.

Particularly preferred targeting moieties are comprised of components of processes involved in plaque formation and growth as well as specific bind partners to such components (e.g. receptors and fragments thereof, receptor ligands (e.g receptor agonists or antagonists), and antibodies and binding fragments thereof). Examples include: (i) cells, including smooth muscle cells, leukocytes, lymphocytes (B-lymphocytes and T-lymphocytes), monocytes, macrophages, foam cells, platelets, erythrocytes and polymorphonuclear cells (e.g. granulocytes and neutrophils) and cellular fragments and analogs thereof (e.g. porphoryins, such as heme and phthalocyanines); (ii) molecules that attract or modify cellular migration including chemotactic proteins and peptides (e.g. monocyte chemotactic protein 1 (MCP-1) and N-formyl-methionyl-leucyl-phenalanine (See U.S. Pat. No. 5,792,444) other formyl peptides; colony stimulating factors (e.g. GM-CSF (See U.S. Pat. Nos. 5,229,496 and 4,879,227) and CSF-1 (See U.S. Pat. Nos. 4,847,201; 4,868,119 and 4,929,700 and receptors and antibodies thereto; and platelet factor 4 (iii) growth factors (e.g. transforming growth factors, e.g. TGF-β, endothelial growth factors (e.g. VEGF) and growth factors that initiate smooth muscle proliferation), (iii) adhesive cell-surface glycoproteins (e.g. E-selectin, VCAM-1 and VCAM1β (See e.g. U.S. Pat. No. 5,272,263) and ICAM-1 (See Rosenfeld, M E et al., Cellularity of Atherosclerotic Lesions *Car. Art. Dis.* 1994; 5:189–197; Navab, M. et al., Monocyte Adhesion and Transmigration in Atherosclerosis. *Cor Art. Dis.* 1994: 5: 198–204) and other cell binding molecules See e.g Kim, J A et al., Partial Characterization of Leukocyte Binding Molecules on Endothelial Cells Induced by Minimally Oxidized LDL *Arterio. Thromb.* 1994; 24: 427–433)); and carbohydrates such as $^{11}$C-deoxy-D-glucose and $^{18}$F-2-fluorodeoxy-D-glucose); (iv) other components of a vascular inflammatory response (for examples complement components (e.g. C1, C1q, C1r, C1s, C2, C3, C3a, C3b, C4, C4C2, C4C2C3b, C5a, C5b and C5a), immunoglobulins and cytokines (e.g. interleukins (e.g. IL-1, (IL-1α (See U.S. Pat. No. 4,762,914) and IL-1β (See U.S. Pat. No. 4,766,061), IL-2 (See U.S. Pat. Nos. 5,037, 644; 4,939,093; 4,604,377; and 4,518,584); IL-3; IL-4 (See U.S. Pat. No. 5,017,691); IL-6; IL-7; and IL-8) interferons (interferon α, interferon γ) and tumor necrosis factors (e.g.

TNF-α); (v) cellular sources of energy for metabolically active plaque formation; (vi) lipids (e.g. liposomes, including polyethylene glycol (PEG) coated liposomes, cholesterol and its esters, lipoproteins (e.g. LDL, HDL, oxidized LDL) and lipid receptors; and (vii) components of the clotting cascade (e.g. fibrin, thrombin, fibrinogen, factor VIII, factor IX, etc.)

In accordance with the invention, the targeting molecule is in association with (spatial proximity to) the label. Spatial proximity between the targeting molecule and the label may be effected in any manner which preserves the specificity of the targeting molecule for its target tissue. For example, spatial proximity between the label and the targeting molecule may be effected by a covalent or non-covalent chemical bond. Such a chemical bond may be effected through a chelating substance and/or an auxiliary molecule such as mannitol, gluconate, glucoheptonate, tartrate, and the like. Alternatively, spatial proximity between the label and the targeting molecule may be effected by incorporating the label and the targeting molecule in a micelle or liposome, in such a way that the affinity of the targeting molecule for its target tissue is maintained. Spatial proximity between the label and the targeting molecule may also be effected by attaching the label and the targeting molecule to a matrix such as a microsphere, liposome, or micelle.

The imaging agents described above may contain any label in accordance with the invention. Highly specific and sensitive labels are provided by radionuclides, which can then be detected, using positron emission tomography (PET) or Single Photon Emission Computed Tomography (SPECT) imaging. More preferably, the imaging agent of the invention contains a radionuclide selected from the group consisting of $^{131}$I, $^{125}$I, $^{123}$I, $^{99m}$Tc, $^{18}$F, $^{68}$Ga, $^{67}$Ga, $^{72}$As, $^{89}$Zr, $^{64}$Cu $^{62}$Cu, $^{111}$In, $^{203}$Pb, $^{198}$Hg, $^{11}$C, $^{97}$Ru, and $^{201}$Tl or a paramagnetic contrast agent, such as gadolinium, cobalt, nickel, manganese and iron. Such labels may be incorporated into the imaging agent by covalent bonding directly to an atom of the targeting molecule, or the label may be non-covalently or covalently associated with the targeting molecule through a chelating structure or through an auxiliary molecule such as mannitol, gluconate, glucoheptonate, tartrate, and the like. When a chelating structure is used to provide spatial proximity between the label and the targeting molecule, the chelating structure may be directly associated with the targeting molecule or it may be associated with the targeting molecule through an auxiliary molecule such as mannitol, gluconate, glucoheptonate, tartrate, and the like.

Any suitable chelating structure may be used to provide spatial proximity between the radionuclide and the targeting molecule of the agent through covalent or noncovalent association. Many such chelating structures are known in the art. Preferably, the chelating structure is an $N_2S_2$ structure, an $NS_3$ structure, an $N_4$ structure, an isonitrile-containing structure, a hydrazine containing structure, a HYNIC (hydrazinonicotinic acid) group-containing structure, a 2-methylthiolnicotinic acid group-containing structure, a carboxylate group containing structure, and the like. In some cases, chelation can be achieved without including a separate chelating structure, because the radionuclide chelates directly to atom(s) in the targeting moiety, for example to oxygen atoms in various moieties.

The chelating structure, auxiliary molecule, or radionuclide may be placed in spatial proximity to any position of the targeting molecule which does not interfere with the interaction of the targeting molecule with its target site in cardiovascular tissue. Accordingly, the chelating structure, auxiliary molecule, or radionuclide may be covalently or non-covalently associated with any moiety of the targeting molecule except the receptor-binding moiety.

Radionuclides may be placed in spatial proximity to the targeting molecule using known procedures which effect or optimize chelation, association, or attachment of the specific radionuclide to ligands. For example, when $^{123}$I is the radionuclide, the imaging agent may be labeled in accordance with the known radioiodination procedures such as direct radioiodination with chloramine T, radioiodination exchange for a halogen or an organometallic group, and the like. When the radionuclide is $^{99m}$Tc, the imaging agent may be labeled using any method suitable for attaching $^{99m}$Tc to a ligand molecule. Preferably, when the radionuclide is $^{99m}$Tc, an auxiliary molecule such as mannitol, gluconate, glucoheptonate, or tartrate is included in the labeling reaction mixture, with or without a chelating structure. More preferably, $^{99m}$Tc is placed in spatial proximity to the targeting molecule by reducing $^{99m}$TcO$_4$ with tin in the presence of mannitol and the targeting molecule. Other reducing agents, including tin tartrate or non-tin reductants such as sodium dithionite, may also be used to make the cardiovascular imaging agent of the invention.

In general, labeling methodologies vary with the choice of radionuclide, the moiety to be labeled and the clinical condition under investigation. Labeling methods using $^{99m}$Tc and $^{111}$In are described for example in Peters, A. M. et al., Lancet 2: 946–949 (1986); Srivastava, S. C. et al., Semin. Nucl. Med. 14(2):68–82 (1984); Sinn, H. et al., Nucl. Med. (Stuttgart) 13:180, 1984); McAfee, J. G. et al., J. Nucl. Med. 17:480–487, 1976; McAfee, J. G. et al., J. Nucl. Med. 17:480–487, 1976; Welch, M. J. et al., J. Nucl. Med. 18:558–562, 1977; McAfee, J. G., et al., Semin. Nucl. Med. 14(2):83, 1984; Thakur, M. L., et al., Semin. Nucl. Med. 14(2):107, 1984; Danpure, H. J. et al., Br. J. Radiol., 54:597–601, 1981; Danpure, H. J. et al., Br. J. Radiol. 55:247–249, 1982; Peters, A. M. et al., J. Nucl. Med. 24:39–44, 1982; Gunter, K. P. et al., Radiology 149:563–566, 1983; and Thakur, M. L. et al., J. Nucl. Med. 26:518–523, 1985.

After the labeling reaction is complete, the reaction mixture may optionally be purified using one or more chromatography steps such as Sep Pack or high performance liquid chromatography (HPLC). Any suitable HPLC system may be used if a purification step is performed, and the yield of cardiovascular imaging agent obtained from the HPLC step may be optimized by varying the parameters of the HPLC system, as is known in the art. Any HPLC parameter may be varied to optimize the yield of the cardiovascular imaging agent of the invention. For example, the Ph may be varied, e.g., raised to decrease the elution time of the peak corresponding to the cardiovascular imaging agent of the invention.

The invention as embodied in a kit for imaging comprises one or more of the imaging agents described above, in combination with a pharmaceutically acceptable carrier such as human serum albumin. Human serum albumin for use in the kit of the invention may be made in any way, for example, through purification of the protein from human serum or though recombinant expression of a vector containing a gene encoding human serum albumin. Other substances may also be used as carriers in accordance with this embodiment of the invention, for example, detergents, dilute alcohols, carbohydrates, auxiliary molecules, and the like. The kit of the invention may of course also contain such other items as may facilitate its use, such as syringes, instructions, reaction vials, and the like.

In one embodiment, a kit according to the invention contains from about 1 to about 30 mCi of the radionuclide-labeled cardiovascular imaging agent described above, in combination with a pharmaceutically acceptable carrier. The cardiovascular imaging agent and carrier may be provided in solution or in lyophilized form. When the cardiovascular imaging agent and carrier of the kit are in lyophilized form, the kit may optionally contain a sterile and physiologically acceptable reconstitution medium such as water, saline, buffered saline, and the like.

In another embodiment, the kit of the invention may contain the unlabeled targeting molecule which has been covalently or non-covalently combined with a chelating agent; an auxiliary molecule such as mannitol, gluconate, glucoheptonate, tartrate, and the like; and a reducing agent such as $SnCl_2$ or tin tartrate. The unlabeled targeting molecule/chelating agent and the auxiliary molecule may be present as separate components of the kit or they may be combined into one kit component. The unlabeled targeting molecule/chelating agent, the auxiliary molecule, and the reducing agent may be provided in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art. When the unlabeled targeting molecule/chelating, agent of this embodiment are in lyophilized form, the kit may optionally contain a sterile and physiologically acceptable reconstitution medium such as water, saline, buffered saline, and the like. The amounts of unlabeled targeting molecule/chelating agent, auxiliary molecule, and reducing agent in this embodiment can be optimized in accordance with the methods for making the cardiovascular imaging agent set forth above. Radionuclides, including, but not limited to, $^{99m}Tc$, e.g. obtained from a commercially available $^{99}Mo/^{99m}Tc$ generator or commercially available $^{123}I$, may be combined with the unlabeled targeting molecule/chelating agent and the reducing agent for a sufficient period of time and at a temperature sufficient to chelate the radionuclide to the targeting molecule/chelating agent, and the imaging agent thus formed is injected into the patient.

The cardiovascular imaging agents of the invention may be used in accordance with the methods of the invention by those of skill in the art, e.g., by specialists in nuclear medicine, to image plaque in the cardiovascular system of a subject. Images are generated by virtue of differences in the spatial distribution of the imaging agents which accumulate in the various tissues and organs of the subject. The spatial distribution of the imaging agent accumulated may be measured using any suitable means, for example, a gamma camera, a PET apparatus, a SPECT apparatus, and the like. Some cardiovascular lesions may be evident when a less intense spot appears within the image, indicating the presence of tissue in which a lower concentration of imaging agent accumulates relative to the concentration of imaging agent which accumulates in surrounding cardiovascular tissue. Alternatively, a cardiovascular lesion might be detectable as a more intense spot within the image, indicating a region of enhanced concentration of the imaging agent at the site of the lesion relative to the concentration of agent which accumulates in surrounding cardiovascular tissue. Thrombi and embolisms are examples of cardiovascular lesions which accumulate enhanced concentrations of the imaging agents of the invention. Accumulation of lower or higher amounts of the imaging at the site of a lesion may readily be detected visually, by inspection of the image of the cardiovascular tissue. Alternatively, the extent of accumulation of the imaging agent may be quantified using known methods for quantifying radioactive emissions. A particularly useful imaging approach employs more than one imaging agent to perform simultaneous studies. For example, simultaneous studies of perfusion and metabolic function would allow study of coupling and uncoupling of flow of metabolism, thus facilitating determinations of tissue viability after a cardiac injury. Such determinations are useful in diagnosis of cardiac ischemia, cardiomyopathy, tissue viability, hibernating heart, and other heart abnormalities.

An effective amount of an imaging agent comprising at least one targeting molecule and a label (e.g. from about 1 to about 50 mCi of a radionuclide) may be combined with a pharmaceutically acceptable carrier for use in imaging studies. In accordance with the invention, "an effective amount" of the imaging agent of the invention is defined as an amount sufficient to yield an acceptable image using equipment which is available for clinical use. An effective amount of the imaging agent of the invention may be administered in more than one injection. Effective amounts of the imaging agent of the invention will vary according to factors such as the degree of susceptibility of the individual, the age, sex, and weight of the individual, idiosyncratic responses of the individual, the dosimetry. Effective amounts of the imaging agent of the invention will also vary according to instrument and film-related factors. Optimization of such factors is well within the level of skill in the art. In general, the effective amount will be in the range of from about 0.1 to about 10 mg by injection or from about 5 to about 100 mg. orally for use with MRI.

As used herein, "pharmaceutically acceptable carrier" includes any and all solvents, dispersion media, coatings, antibacterial and antifungal agents, isotonic agents, absorption delaying agents, and the like. The formulation used in the present invention may also contain stabilizers, preservatives, buffers, antioxidants, or other additives known to those of skill in the art. The use of such media and agents for pharmaceutically active substances is well known in the art. Supplementary active compounds can also be incorporated into the imaging agent or the invention. The imaging agent of the invention may further be administered to an individual in an appropriate diluent or adjuvant, co-administered with enzyme inhibitors or in an appropriate carrier such as human serum albumin or liposomes. Pharmaceutically acceptable diluents include sterile saline and other aqueous buffer solutions. Adjuvants contemplated herein include resorcinols, non-ionic surfactants such as polyoxyethylene oleyl ether and n-hexadecyl polyethylene ether. Enzyme inhibitors include pancreatic trypsin inhibitor, diethylpyrocarbonate, and trasylol. Liposomes inhibitors include water-in-oil-in-water CGF emulsions as well as conventional liposomes (Strejan et al., J Neuroimmunol 7:27 [1984]).

The subject imaging agents can be administered to a subject in accordance with any means that facilitates accumulation of the agent in a subject's cardiovascular system. Preferably, the imaging agent of the invention is administered by arterial or venous injection, and has been formulated as a sterile, pyrogen-free, parenterally acceptable aqueous solution. The preparation of such parenterally acceptable solutions, having due regard to pH, isotonicity, stability, and the like, is within the skill in the art. A preferred formulation for intravenous injection should contain, in addition to the cardiovascular imaging agent, an isotonic vehicle such as Sodium Chloride Injection, Ringer's Injection, Dextrose Injection, Dextrose and Sodium Chloride Injection, Lactated Ringer's Injection, or other vehicle as known in the art.

The amount of imaging agent used for diagnostic purposes and the duration of the imaging study will depend upon the nature and severity of the condition being treated, on the nature of therapeutic treatments which the patient has undergone, and on the idiosyncratic responses of the patient. Ultimately, the attending physician will decide the amount of imaging agent to administer to each individual patient and the duration of the imaging study.

The present invention is further illustrated by the following examples, which should not be construed as limiting in any way. The contents of all cited references (including literature references, issued patents, published patent applications) as cited throughout this application are hereby expressly incorporated by reference.

EXAMPLE

Preparation of Radiolabeled Chemotactic Peptide For-MLF

For-MLF is a bacterial product that initiates leukocyte chemotaxis by binding to high affinity receptors on white blood cell membranes (Showell et al., J Exp Med 143: 1154–1169 [1976], Schiffmann et al., Proc Natl Acad Sci USA 72:1059–1062 [1975], Williams et al., Proc Natl Acad Sci 74:1204–1208 [1977]). These receptors are present on both polymorphonuclear leukocytes and mononuclear phagocytes. Due to the very small size of For-MLF (MW 437), its molecular structure can be readily manipulated to design an optimal imaging agent.

The labelled chemotactic peptide can be synthesized and purified by the techniques described in Babich et al., J Nucl Med 34:1964–1974 (1993).

Dimethylformamide (DMF) (2 ml) and 60 µl of diisopropylethylamine is added to 186 mg of N-For-Met-Leu-Phe-diaminohexyl amide followed by 154 mg succinimidyl-6-t-BOC-hydrazinopyridine-3-carboxylic acid in 1 ml DMF. The mixture becomes yellow and the peptide dissolves within a short time. After 2 hours, ether is added to the reaction mixture and the upper layer is discarded. Water is added to the oily residue causing a solid to form. The solid is washed with 5% sodium bicarbonate, water and ethyl acetate, and the yield is determined. The t-BOC protecting group is removed by stirring the crude product with 5 ml of trifluoroacetic acid (TFA) containing 0.1 ml of p-cresol for 15 min. at 20° C. Prolonged treatment with TFA results in increased levels of a side product. The TFA is removed by rotary evaporation, and ether is added to the residue to precipitate the deprotected peptide. The product is purified by reverse phase HPLC on a 2.5×50 cm Whatman ODS-3 column is eluted with a gradient of acetonitrile in 0.1% TFA. Fractions containing the major component is combined and the solvent is removed to yield the desired product.

Technetium-99m-pertechnetate ($^{99}$Mo/$^{99m}$Tc generator) and stannous glucoheptonate (Glucoscan) are obtained from New England Nuclear (Boston, Mass.). Technetium-99m-glucoheptonate is used to provide the necessary Tc(V) oxo species for radiolabeling the hydrazinonicotinamide conjugated peptides. Approximately 2.S ml of $^{99m}$Tc-pertechnetate in 0.9% of NaCl is added to the freeze-dried kit. The final radioactive concentration is 5–10 mCi/ml and radiochemical purity of the product is determined by instant thin-layer silica gel chromatography (ITLC-sg) using both acetone and 0.9% NaCl as mobile phase solvents.

Approximately 0.2 mg of peptide is dissolved in 50 µl dimethylsulfoxide and the solution is diluted to a final concentration of 0.1 mg/ml with 0.1 M acetate buffer pH 5.2. Peptide solution (0.5 ml) is placed in a clean glass vial and 0.5 ml of $^{99m}$Tc-glucoheptonate is added. The mixture is vortexed briefly and is allowed to stand at room temperature for 1 hour. Radiochemical purity is determined by ITLC-sg in three solvent systems: acetone, 0.9% NaCl, and acetone and water (9:1).

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A cardiovascular imaging agent comprising a radionuclide, said radionuclide being chemically bonded to a targeting moiety comprising a component of a process involved in plaque formation, wherein the targeting moiety is fibrin, thrombin, fibrinogen, factor VIII, or factor IX, wherein said radionuclide is a positron emitting radionuclide selected from the following: $^{18}$F, $^{68}$Ga, $^{62}$Cu, or radioactive isotopes of iodine.

2. The agent of claim 1, wherein said plaque is an atherosclerotic forming plaque.

3. A method of imaging cardiovascular plaque formation in a mammal, comprising administering to the mammal a cardiovascular imaging agent having a radionuclide, said radionuclide being chemically bonded to a targeting moiety comprising a component of a process involved in plaque formation, wherein the targeting moiety is fibrin, thrombin, fibrinogen, factor VIII, or factor IX, wherein said radionuclide is a positron emitting radionuclide selected from the following: $^{18}$F, $^{68}$Ga, $^{62}$Cu, or radioactive isotopes of iodine.

4. The method of claim 3, wherein the method detects a cardiovascular lesion in a mammal, said method comprising the steps of administering to the mammal said imaging agent, detecting the spatial distribution of said agent accumulated in the mammal's cardiovascular system, wherein a detected accumulation of said agent in a region which is different from the detected accumulation of said agent in other regions is indicative of a lesion.

5. The method of claim 4, wherein said cardiovascular lesion is an atherosclerotic forming lesion.

6. A kit for cardiovascular imaging, comprising a supply of the imaging agent or a precursor of the imaging agent having a radionuclide, said radionuclide being chemically bonded to a targeting moiety comprising a component of a process involved in plaque formation, wherein the targeting moiety is fibrin, thrombin, fibrinogen, factor VIII, or factor IX, wherein said radionuclide is a positron emitting radionuclide selected from the following: $^{18}$F, $^{68}$Ga, $^{62}$Cu, or radioactive isotopes of iodine.

* * * * *

UNITED STATES PATENT AND TRADEMARK OFFICE
CERTIFICATE OF CORRECTION

PATENT NO. : 7,060,251 B1 Page 1 of 1
APPLICATION NO. : 09/530818
DATED : June 13, 2006
INVENTOR(S) : David R. Elmaleh, Alan J. Fischman and John W. Babich It is certified that error appears in the above-identified patent and that said Letters Patent is hereby corrected as shown below:

On the Title page, please insert Item --(63) Continuation of application No. 08/925,213, filed Sep. 8, 1997, now abandoned.--.

Signed and Sealed this

Twenty-third Day of June, 2009

JOHN DOLL
*Acting Director of the United States Patent and Trademark Office*